United States Patent

Bhagavathula et al.

(10) Patent No.: US 6,954,146 B2
(45) Date of Patent: Oct. 11, 2005

(54) METHOD FOR DETERMINING A STATE OF A ROAD DURING THE DRIVING MODE OF A MOTOR VEHICLE

(75) Inventors: Seshu Bhagavathula, Waldenbuch (DE); Shanmukh Katragadda, Bangalore (IN); Ravindra Peravali, Ulm (DE); Juergen Trost, Grafenberg (DE)

(73) Assignee: DaimlerChrysler AG, Stuttgart (DE)

( * ) Notice: Subject to any disclaimer, the term of this patent is extended or adjusted under 35 U.S.C. 154(b) by 73 days.

(21) Appl. No.: 10/738,135

(22) Filed: Dec. 18, 2003

(65) Prior Publication Data

US 2004/0212516 A1 Oct. 28, 2004

(30) Foreign Application Priority Data

Dec. 19, 2002 (DE) .......................... 102 59 979

(51) Int. Cl.[7] .................. G01N 19/02; G01N 29/12; B60Q 1/00; G01B 21/30; G01H 17/00
(52) U.S. Cl. .................. 340/566; 340/580; 340/581; 340/582; 340/583; 340/901; 340/905; 73/590; 73/594; 73/648; 73/649; 73/660; 73/659; 180/167; 180/168; 180/169; 364/550; 364/551.01; 701/80
(58) Field of Search ................. 340/580–583, 340/601–602, 901, 905; 701/80; 364/550, 551.01; 73/593, 645–660; 180/167

(56) References Cited

U.S. PATENT DOCUMENTS 5,532,678 A * 7/1996 Kin et al. .................... 340/438
5,586,028 A * 12/1996 Sekine et al. ................. 701/1
5,852,243 A * 12/1998 Chang et al. ................. 73/659

FOREIGN PATENT DOCUMENTS

| DE | 3728708 | 3/1989 |
|----|---------|--------|
| DE | 40 19 501 A1 | 6/1990 |
| DE | 40 40 842 A1 | 12/1990 |
| DE | 42 13 221 C2 | 4/1992 |
| DE | 4213221 | 10/1993 |
| DE | 1998 55 332 A1 | 12/1998 |
| EP | 0 412 791 A2 | 2/1991 |
| JP | 8-175334 | 7/1996 |
| JP | 8-261993 | 10/1996 |

* cited by examiner

Primary Examiner—Jeffery Hofsass
Assistant Examiner—Lam Pham
(74) Attorney, Agent, or Firm—Crowell & Moring LLP

(57) ABSTRACT

In a method for determining the state of a road during driving of a motor vehicle, the sound which is generated when a vehicle tire rolls on an underlying surface is sensed. A frequency signal is determined by means of a sound level signal which describes the sound, and is divided into at least two sub-zones by means of at least one limiting frequency. The sub-zones are each assigned to an associated frequency band, and an intensity value is determined for each of at least two frequency bands from the assigned sub-zone of the frequency signal. The intensity value is characteristic of the sound intensity which is present in a frequency band. An intensity ratio is formed from two intensity values by dividing the first intensity value of the first frequency band by the second intensity value of the second frequency band, and is used to determine the state of a road.

10 Claims, 1 Drawing Sheet

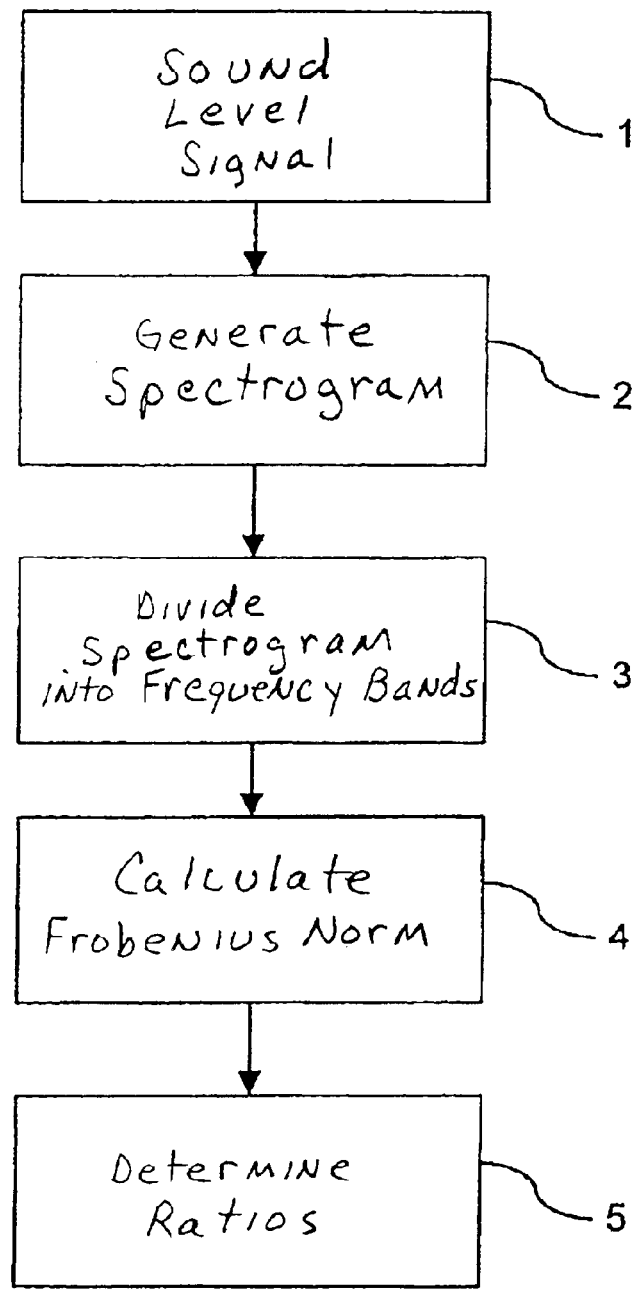
Figure

METHOD FOR DETERMINING A STATE OF A ROAD DURING THE DRIVING MODE OF A MOTOR VEHICLE

BACKGROUND AND SUMMARY OF THE INVENTION

This application claims the priority of German patent document 102 59 979.3, filed 19 Dec. 2002, the disclosure of which is expressly incorporated by reference herein.

The present invention relates to a method for determining the state of a road during driving of a motor vehicle.

German patent document DE 42 13 221 C2 discloses a method for determining the degree of wetting of an underlying road surface, without contacting it. A sound pickup is used to sense the noise of spray water or the rolling noise of at least one wheel of the vehicle, and generates an output signal which corresponds to the sensed noise. The spectral distribution of the sensed noise is determined from this output signal by means of a Fourier transformation, and a frequency band is cut out from the spectral distribution. The average amplitude of the spectral distribution within the frequency band is calculated, and a value for wetting of the underlying surface is assigned to the average value by means of a characteristic diagram. A further variable such as, for example, vehicle speed, engine speed, steering angle, tire type, tire temperature, tire pressure or load state can be taken into account as correction variables. In addition, background noise such as the engine noise of the drive engine can be determined and compensated.

One object of the invention is to permit more precise and reliable determination of the state of the road surface during driving of a motor vehicle.

This and other objects and advantages are achieved by the method according to the invention, which determines the state of the road surface by taking advantage of the phenomenon that various noises are generated when a vehicle rolls on an underlying surface, including not only the actual rolling noise produced by the direct contact between the tire of the vehicle and the underlying surface, but also, for example, additional wind noises which are produced by the relative movement between the ambient air and the wheel of the vehicle, or the sounds of spray water which are produced as a result of an impact of the water droplets sprayed from the tire onto a component of the vehicle. The sound of these various superimposed noises is sensed and a sound level signal is generated which describes the sensed sound. The sound level signal can be generated with any suitable sound pickup such as, for example, a microphone or some other vibration pickup. Depending on the type of the sound pickup and its mounting location, the various noises are weighted to differing degrees, filtered due to the sound transmission link and possibly additionally accompanied by numerous background noises. In order to feed as far as possible only the desired noise or noises (in particular the actual rolling noise) to a processor for further evaluation, filtering or some other conditioning of the sound level signal may take place. However, this is not absolutely necessary.

Based on the sound level signal (in particular of a chronologically limited section of the sound level signal) a frequency signal which describes the chronologically limited section of the sound level signal is then determined. This may be carried out, for example, by means of a discrete Fourier transformation. The frequency signal is divided into various sub-zones by means of at least one limiting frequency. Each of these sub-zones is assigned to an associated frequency band in each case. An intensity value is determined for each of at least two frequency bands from assigned sub-zones of the frequency signal, such intensity value being characteristic of the sound intensity which is present within the assigned frequency band and, if appropriate, within a predefinable chronological section. An intensity ratio is determined from two intensity values by dividing a first intensity value of a first frequency band by a second intensity value of a second frequency band.

A plurality of intensity ratios can be determined as a function of the number of intensity values. It is possible, for example, to use arithmetic or geometric amplitude average values, other weighted average values or autocorrelation values of the frequency signal as intensity values. It is also possible to take into account the standard deviation or the variance of the frequency signal in order to determine the intensity values. The intensity ratios which are acquired from the intensity values are used to determine the state of a road. The covering which is present on the road surface or whether the road is wet, for example, is determined as a state of a road.

In order to determine the state of a road it is also possible to sense and use further variables, for example the outside temperature or variables relating to the dynamics of vehicle movement.

An advantage of the method according to the invention is that the state of the road can be determined precisely and reliably. The method according to the invention is additionally very robust with respect to interference and is independent of, or at least largely insensitive to, a change in a large number of further parameters, for example the velocity of the vehicle, the load of the vehicle, the type of tire, the profile depth or the tire pressure.

In one advantageous embodiment of the invention, a comparison is made between at least one determined intensity ratio and a predefinable value range. The result of the comparison is used to determine the state of the road, in particular the state of the road is determined directly by means of this comparison, i.e. without further variables. In a subsequent step, further variables can be used to obtain more precise information on the directly determined state of the road or verify it.

In a simple embodiment it is possible, without taking into account further variables, to determine the state of the road merely by comparing a determined intensity ratio with a predefinable value range and without carrying out further subsequent evaluation steps. For this purpose it is possible to predefine an assignment of a road state to a value range of the intensity ratio of the intensity values of two frequency bands. An advantage of this embodiment is the possibility of determining the state of the road very quickly and easily.

Instead of the comparison between an intensity ratio and one or more predefinable value ranges it is possible to compare a plurality of determined intensity ratios with a plurality of predefinable value ranges. The comparison results are used to determine the state of the road, in particular in one simple embodiment conclusions about the state of the road are drawn directly from the comparison results.

In another advantageous embodiment of the invention, a spectrogram is determined as the frequency signal. The spectrogram is divided into at least two frequency bands by means of at least one limiting frequency. A weighted average value of the spectral energy distribution contained in the frequency band can be determined as an intensity value for a frequency band. Conclusions are then in turn drawn about the state of the road from the ratio of the intensity values of the two frequency bands. This technique permits more precise and reliable determination of the state of the road, which additionally permits time-dependent effects to be taken into account if the spectrogram has a corresponding chronological resolution.

In still another embodiment of the invention, a quadratic matrix is determined for at least one frequency band. Each element of this matrix is assigned a frequency sub-band (a predefinable range of the frequency domain and a time subsection, i.e., a predefinable range in time). One element of the matrix is characteristic of the intensity of the frequency signal in the frequency sub-band assigned to the matrix element, and in the time subsection assigned to the matrix element. The norm of a matrix is determined as an intensity value. Such a quadratic matrix is preferably determined for each of the frequency bands predefined by the limiting frequencies, and the respective norm for said matrices is determined from the matrices as intensity values. The Frobenius norm is preferably determined as the norm of the matrices.

Such a matrix may be constructed in such a way that, for example, the frequency band from 0 to 99 Hz is assigned to row 1, the frequency sub-band from 10 to 199 Hz is assigned to row 2, the frequency sub-band from 200 to 299 Hz is assigned to row 3, etc. In a comparable way, the time subsection from $t_0$ to $t_0+10$ ms is assigned to column 1, the time subsection from $t_0+5$ ms to $t_0+15$ ms is assigned to column 2 and the time subsection from $t_0+10$ ms to $t_0+20$ is assigned to column 3, etc.

The time periods which are assigned to the columns may overlap, adjoin one another or be arranged with gaps. An inverted arrangement of the sequence of the rows or columns or interchanging the rows with the columns does not have any fundamental effect on the method according to the invention, and is therefore possible.

If the frequency signal is divided by n limiting frequencies, n+1 matrices are generated and an intensity value is determined for each matrix. The intensity ratios are determined from the n+1 intensity values by forming quotients. The intensity ratios are used to determine the state of the road.

An advantage of this embodiment of the invention is that, to a significant degree, the effects which bring about nonsteady-state behavior and transient recovery effects during the generation of sound between the underlying surface and tire can be completely eliminated or at least reduced.

In one embodiment, each frequency band is divided into $2^k$ frequency sub-bands, k being a natural number. In addition, the time section which is assigned to a matrix is divided into $2^k$ time subsections. As a result, a matrix comprises $2^k$ columns and $2^k$ rows. This permits the norms of the matrices to be determined easily and efficiently, and thus permits the state of the road to be determined rapidly.

k is preferably greater than 1, which increases the precision and/or the reliability of the determination of the state of the road. However, unnecessarily large values for k are to be avoided in order to reduce the computational complexity.

In an advantageous embodiment of the invention, in each case the determined intensity ratios of adjacent frequency bands are used to determine the state of the road. As a result, the states of the road, for example the detection of different thicknesses of water film on the underlying surface or the detection of different degrees of roughness of the underlying surface, can be satisfactorily separated.

In order to simplify the determination of the state of the road it is advantageous for all the frequency bands which can be predefined by the one or more limiting frequencies to have the same bandwidth.

If a plurality of intensity ratios are used to determine the state of the road, a refined and/or more precise determination of the state of the road is possible. For example, when the frequency signal is divided into four frequency bands A, B, C, D, the intensity ratios $I_A/I_B$, $I_B/I_C$, $I_C/I_D$, and possibly in addition the intensity ratios $I_A/I_C$, $I_A/I_D$ and $I_B/I_D$, can be used to determine the state of the road.

It is possible, for example, to determine the thickness of a water film located on the underlying surface, the aggregate states of snow or ice, the nature of the underlying surface, and in particular the maximum possible coefficient of friction, as the state of the road. It is possible to distinguish between different road coverings, such as asphalt, concrete and cobblestone pavement. It is particularly advantageous to detect the thickness of a film of water which wets the road pavement as the maximum possible coefficient of friction between the tire and underlying surface depends greatly on the thickness of wetting.

Because the method according to the invention is not a computationally complex, and thus requires only a short computing time, it may be carried out very rapidly so that the state of the road which is determined is available virtually without a time delay, i.e. in real time.

Other objects, advantages and novel features of the present invention will become apparent from the following detailed description of the invention when considered in conjunction with the accompanying drawings.

BRIEF DESCRIPTION OF THE DRAWINGS

The FIGURE shows a flowchart of an advantageous embodiment of the method according to the invention.

DETAILED DESCRIPTION OF THE DRAWINGS

Referring to the FIGURE, in step 1, the sound which is generated when a vehicle rolls on the underlying surface is sensed and a sound level signal which describes the sensed sound is generated. The sound is sensed by means of a sound pickup arranged in the wheel case or near to the tire. The sound level signal which describes the sound is, for example, the output signal of the sound pickup, the amplitude of the sound level signal being proportional to the sound amplitude. The sound level signal has a predefinable frequency bandwidth which is, for example, 8 kHz.

In step 2, a chronologically limited section of the sound level signal is divided into a plurality of predefinable time subsections. A power spectrum is calculated for each of the time subsections. The power spectrum can be calculated by means of the following equation:

$$P(t, \omega) = \left| \frac{1}{\sqrt{2\pi}} \int e^{-j\omega\tau} s(\tau) h(t-\tau) d\tau \right|^2$$

where $S(\tau)$ is the sound level signal and $h(t)$ is a window function by means of which the time subsections are predefined.

A spectrogram is obtained from the power spectrum by displacing the time window of the window function incrementally and plotting the obtained power spectra in succession.

The analog function of the power spectrum is discretized in the frequency domain, i.e. it is divided into predefinable subsections assigned to a frequency sub-band in the frequency domain. The signal amplitude is averaged within a subsection, and the average value is allocated to the subsection.

In an alternative embodiment, the sound level signal is already a digitized signal which can be generated by means of an analog/digital converter. In this case, the discrete spectrogram is calculated by means of a summation which corresponds to the specified integration.

As a result of step 2, a spectrogram is obtained which has, as matrix elements, in each case a numerical value for the sound intensity which is present within a time subsection and within a frequency sub-band.

The time subsections and frequency sub-bands may be predefined in such a way that adjacent time subsections or adjacent frequency sub-bands overlap, adjoin one another, or there is an intermediate space between adjacent time subsections or frequency sub-bands.

In step 3, the frequency signal, i.e. the discrete spectrogram which is now present, is divided into $2^k$ frequency bands by means of $2^k-1$ limiting frequencies. The limiting frequencies are arranged equidistantly in the frequency domain. For example, the spectrogram may be divided into four frequency bands (and thus into four submatrices) by means of three limiting frequencies. The number of frequency bands, the number of frequency sub-bands and the number of time subsections are predefined such that each submatrix is quadratic (i.e., contains the same number of rows as columns).

In step 4, the Frobenius norm is calculated for each submatrix as a value which characterizes the sound intensity within the associated frequency band:

$$\|X\| = \sqrt{Spur(X^T X)} = \sqrt{\sum_{i=1}^{m} \sum_{j=1}^{n} |x_{ij}|^2}$$

In step 5, the ratios of the Frobenius norms of the four submatrices, i.e., the intensity ratios $X_N/X_{N+1}$ of the intensity values of the four frequency bands are formed.

To determine the state of a road, the intensity ratios are compared with predefinable intensity ratio ranges which are stored in a table. A predefinable intensity ratio range is assigned, by means of the table, to one predefinable state of a road or one predefinable feature of the state of a road or one predefinable maximum coefficient of friction in each case.

Instead of a table, it is also possible to predefine any other known manner of assignment between the state of a road or features describing it and the intensity ratios determined. It is possible, for example, to predefine a functional assignment, in particular a threshold value function.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for determining the state of a road during driving of a motor vehicle, comprising:

sensing at least a portion of a sound generated when a vehicle tire rolls on an underlying road surface being sensed;

generating a sound level signal which describes said sound, using said at least a portion; and determining a frequency signal which characterizes the sound level signal; wherein the frequency signal is divided, by means of at least one limiting frequency, into at least two sub-zones which are each assigned to an associated frequency band;

an intensity value is determined for each of at least two frequency bands from the assigned sub-zone of the frequency signal, said intensity value being characteristic of the sound intensity present in a frequency band;

an intensity ratio is formed by dividing a first intensity value of a first frequency band by a second intensity value of a second frequency band; and the intensity ratio is used to determine the state of the road.

2. The method as claimed in claim 1, wherein the frequency signal is determined on the basis of a chronologically limited section of the sound level signal.

3. The method as claimed in claim 1, wherein to determine the state of the road, at least one determined intensity ratio is compared with a predefinable value range assigned to a road state; and the actual state of the road is determined based on this comparison.

4. The method as claimed in claim 1, wherein the frequency signal comprises a spectrogram.

5. The method as claimed in claim 1, wherein a quadratic matrix is determined for a frequency band, a matrix element being characteristic of the intensity of the sensed sound level signal within a predefinable frequency sub-band and within a predefinable time subsection; and the norm of the matrix is determined as an intensity value.

6. The method as claimed in claim 5, wherein the matrix has $2^k$ rows and $2^k$ columns, k being an integer.

7. The method as claimed in claim 1, wherein intensity ratios are determined for each pair of adjacent frequency bands and used to determine the road state.

8. The method as claimed in claim 1, wherein each of the frequency bands has the same bandwidth.

9. The method as claimed in claim 1, wherein at least one of thickness of a film of water on the underlying surface, presence of snow or ice on the underlying surface and type of covering of the underlying surface is determined as a road state.

10. The method as claimed in claim 1, wherein a maximum possible coefficient of friction between the underlying surface and the vehicle tires is determined as a road state.

* * * * *